(12) United States Patent
Tucker et al.

(10) Patent No.: US 10,610,121 B1
(45) Date of Patent: Apr. 7, 2020

(54) METHOD FOR DESYNCHRONIZING PATHOLOGICAL NEURAL OSCILLATIONS

(71) Applicant: Brain Electrophysiology Laboratory Company, LLc, Eugene, OR (US)

(72) Inventors: Don M. Tucker, Eugene, OR (US); Phan Luu, Eugene, OR (US)

(73) Assignee: Brain Electrophysiology Laboratory Company, LLC, Eugene, OR (US)

( * ) Notice: Subject to any disclaimer, the term of this patent is extended or adjusted under 35 U.S.C. 154(b) by 0 days.

(21) Appl. No.: 16/540,507

(22) Filed: Aug. 14, 2019

(51) Int. Cl.
| | |
|---|---|
| *A61B 5/0476* | (2006.01) |
| *A61B 5/053* | (2006.01) |
| *A61B 5/055* | (2006.01) |
| *A61B 6/03* | (2006.01) |
| *A61N 1/36* | (2006.01) |

(52) U.S. Cl.
CPC ............ *A61B 5/0476* (2013.01); *A61B 5/055* (2013.01); *A61B 5/0536* (2013.01); *A61B 6/032* (2013.01); *A61N 1/36025* (2013.01)

(58) Field of Classification Search
CPC ..... A61B 5/0476; A61B 5/0536; A61B 5/055; A61B 6/032; A61N 1/36025
See application file for complete search history.

(56) References Cited

U.S. PATENT DOCUMENTS 6,594,531 B2   7/2003  Eshelman
8,583,238 B1 * 11/2013  Heldman ............. A61N 1/0492
                                                 607/45

OTHER PUBLICATIONS

Oleksandr V. Popovych and Peter A. Tass; "Desynchronizing electrical and sensory coordinated reset neuromodulation;" Frontiers in Human Neuroscience, Mar. 20, 2012.
Peter A. Tess, et al; "Coordinated Reset Has Sustained Aftereffects in Parkinsonian Monkeys;" Brief Communication; Annals of Neurology, Nov. 2012.
Jacek P. Dmochowski et al; "The Point Spread Function of the Human Head and its Implications for Transcranial Current Stimulation;" City College of New York, Department of . . . Biomedical Engineering, date of publication not indicated.
Yu Huang et al; "Optimized Interferential Stimulation of Human Brains;" City College of the City University of New York, Department of Biomedical Engineering, . . . bioRxiv preprint first posted online Sep. 26, 2019.

* cited by examiner

*Primary Examiner* — Michael T Rozanski
(74) *Attorney, Agent, or Firm* — Birdwell & Janke, LLP

(57) ABSTRACT

A method for desynchronizing a pathological neural oscillations, includes identifying a first subpopulation of the neurons involved in the pathological neural oscillation that are in alignment with each other within a predetermined angular stimulation range, and a second subpopulation that are both (A) in alignment with each other within the predetermined angular stimulation range, and (B) out of alignment with the first neurons by at least the predetermined angular stimulation range, and applying electrical stimuli to the first and second subpopulations through scalp electrodes, the electrical stimuli being out of phase with the pathological neural oscillations for desynchronizing the pathological neural oscillations.

8 Claims, 3 Drawing Sheets

ＭMETHOD FOR DESYNCHRONIZING PATHOLOGICAL NEURAL OSCILLATIONS

FIELD OF INVENTION

The present invention relates to non-invasive methods for desynchronizing pathological neural oscillations in the brain, such occur in Parkinson's disease.

BACKGROUND

Pathological neural oscillations in the brain have been successfully disrupted in the prior art by stimulating nerve endings outside of the brain, such as by tactile stimulation of the fingertips, visual stimulation of the optic nerves, or acoustic stimulation of the auditory nerves. Such disruptions have also been achieved in the prior art by use of current-injecting electrodes implanted in the subthalamic nucleus (STN) of the brain.

Synchronous oscillations of a global or "target" population of neurons are disrupted by differentially stimulating subsets or "subpopulations" of the target. More specifically, each of at least two subpopulations is stimulated to oscillate in synchrony with an applied stimulus that is desynchronized (typically by being out of phase) with the target as well as with the stimuli applied to the other subpopulations being (or to be) stimulated. The stimuli are typically applied to the at least two subpopulations in a repetitive temporal sequence to produce a desynchronization of the target that is semi-permanent.

It is an object of the invention to provide an alternative and potentially less invasive and more effective method for achieving such desynchronization.

SUMMARY

Disclosed is a method for desynchronizing a pathological neural oscillation in the brain of a subject. The basic method includes identifying a first contiguous subset of the cortex wherein first neurons involved in the pathological neural oscillation are in alignment with each other within a predetermined angular stimulation range; identifying a second contiguous subset of the cortex, distinct from the first contiguous subset of the cortex, wherein second neurons that are also involved in the pathological neural oscillation are both (A) in alignment with each other within the predetermined angular stimulation range, and (B) out of alignment with the first neurons by at least the predetermined angular stimulation range; applying, through a first set of scalp electrodes, a first electrical stimulus to the first subset of the cortex that is in alignment with the first neurons within the predetermined angular range, and which is out of phase with the pathological neural oscillations; and applying, through a second set of scalp electrodes, a second electrical stimulus to the second subset of the cortex that is in alignment with the second neurons within the predetermined angular range, and which is out of phase with the pathological neural oscillations, wherein the steps of applying the first and second stimuli are sufficient to desynchronize the pathological neural oscillation.

Optionally, the second electrical stimulus may be out of phase with the first electrical stimulus.

Optionally, the first and second electrical stimuli may be applied during overlapping times.

Optionally, at least one of the steps of identifying contiguous subsets of the cortex may include obtaining an electroencephalographic signature of the pathological neural oscillation.

Optionally, the method may include creating a model of electrical properties of the subject's head, and utilizing the model for determining at least one of the first and second electrical stimuli.

Optionally, the step of creating a model of electrical properties of the subject's head may include combining data obtained from magnetic resonance imaging, X-ray computed tomography, and electrical impedance tomography performed on the subject's head.

Optionally, the method may include obtaining a magnetic resonance image of the subject's head, and utilizing the magnetic resonance image for predetermining, relative to the step of applying the first electrical stimulus, whether the first neurons satisfy criterion (A).

Optionally, the magnetic resonance image may also be used for predetermining, relative to the step of applying the second electrical stimulus, whether the second neurons satisfy both criteria (A) and (B).

It is to be understood that this summary is provided as a means of generally determining what follows in the drawings and detailed description and is not intended to limit the scope of the invention. Objects, features and advantages of the invention will be readily understood upon consideration of the following detailed description taken in conjunction with the accompanying drawings.

DESCRIPTION OF PREFERRED EMBODIMENTS

The present invention provides a method for disrupting pathological neural oscillations in the brain, such as occur in Parkinson's disease, that makes use of what is known in the art of neuroscience as transcranial electrical stimulation ("TES").

Figure 1:
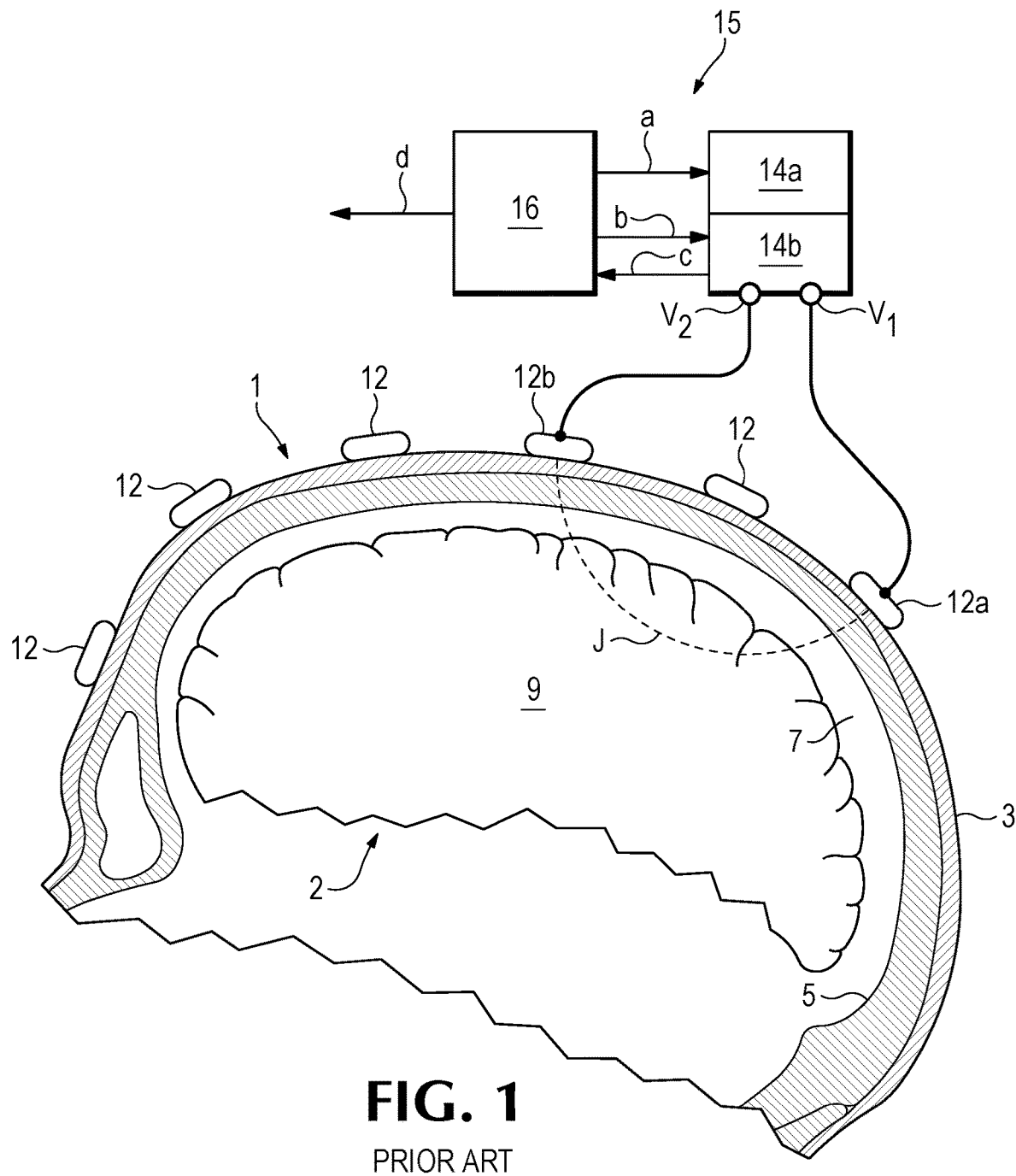
FIG. 1 is a schematic diagram of a system for performing transcranial electrical stimulation of a subject's brain, such as is ordinarily provided in the prior art, and which may be used for practicing methods according to the present invention.

Referring to FIG. 1, TES is well known prior art and need not be discussed in great detail. Basically, it employs electrodes 12 placed in electrical contact with the skin of a subject or patient's scalp, for non-invasively injecting electrical currents into the subject's head 1 for stimulating the subject's brain 2. Specifically, for each of a number of different pairs of scalp electrodes, an electrical current "J" flows from one of the electrodes 12a held at a first electrical potential "$V_1$," to another of the electrodes 12b held at a second electrical potential "$V_2$," first through the subject's scalp 3, thence through the subject's skull 5, thence through the subject's cerebrospinal fluid 7, and thence through the subject's cortex 9.

The electrical potentials $V_1$ and $V_2$ may be produced by a system 15 comprising a standard multi-channel voltage source 14a (each pair of electrodes defining a channel, the other channels and connections to the electrodes 12 not shown) controlled (arrow "a") by a controller 16 which may be a standard programmable computer such as a PC or Macintosh.

Figure 2:
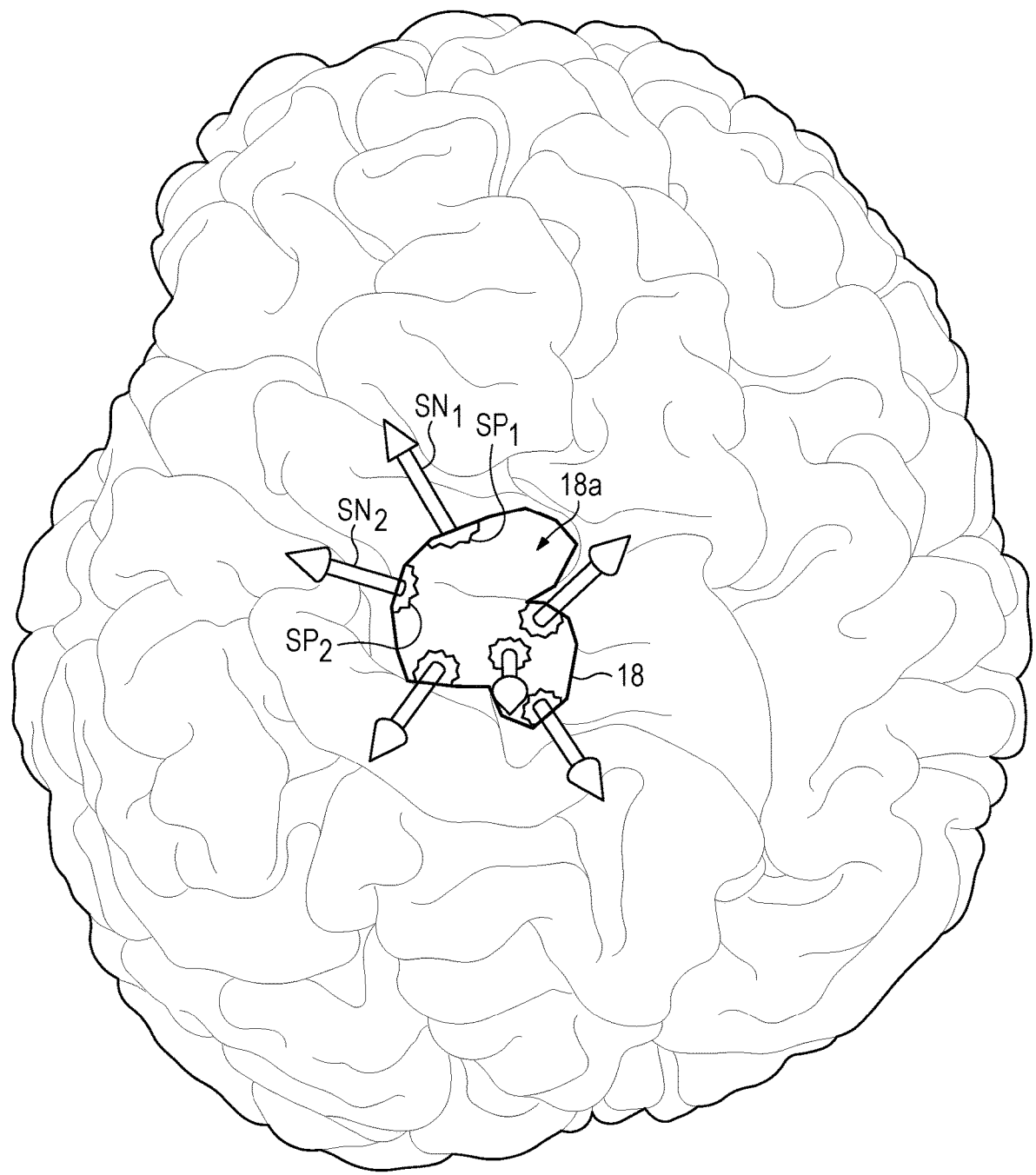
FIG. 2 is an isometric view of a brain, showing a portion of the cortex that is involved in a pathological neural oscillation and identified as a target for stimulation, for desynchronizing the pathological neural oscillation according to the invention.
Figure 3:
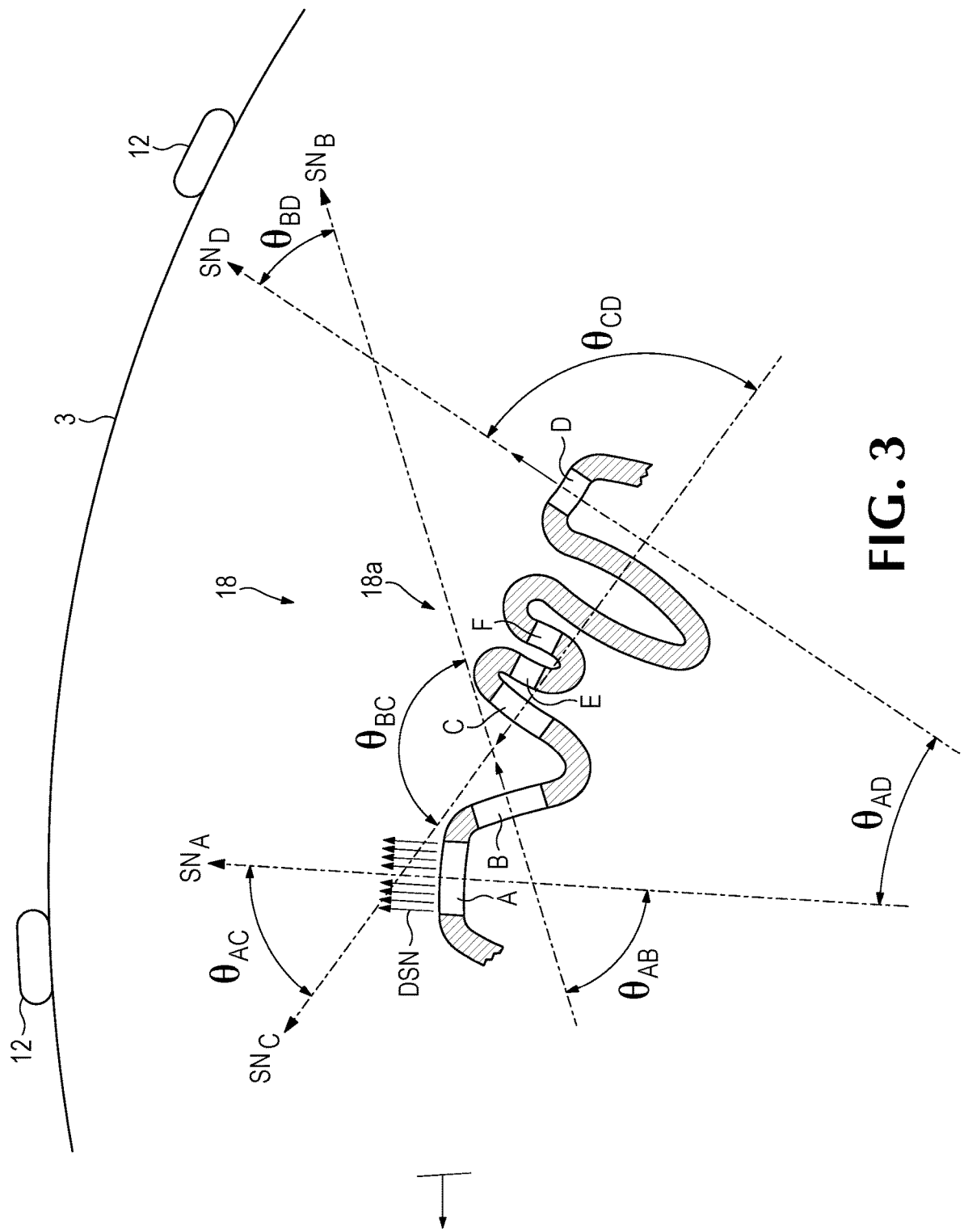
FIG. 3 is a simplified side elevation of the brain of FIG. 2 located beneath the subject's scalp, showing the portion of the cortex in section.

FIGS. 2 and 3 show a portion of the subject's cortex which has been identified as a desired target 18 for desynchronization according to the invention. Such a target may be identified in any manner known in the art, such as from electroencephalographic ("EEG") signatures and/or a priori anatomical knowledge. With particular reference to FIG. 3, for obtaining EEG signatures, the same electrodes 12 that are used for stimulation can be used as sensors of the electrical potentials generated by the brain as is known in the art. In such case, the system 15 would include a standard multi-channel voltage measuring device 14b, and the controller 16 may be adapted accordingly for controlling the voltage measuring device to measure electrical potentials (arrow "b") sensed by the electrodes 12, and to send the measured data (arrow "c") to the controller 16, so that the controller 16 may analyze the measured data and/or output the data (arrow "d") for analysis by another device (e.g., a separate computer).

The identified target may further be imaged by any means known in the art, such as by magnetic resonance imaging ("MRI"). The image may be used to conceptually subdivide the target into a number of different subpopulations, such as those referenced as "$SP_1$" and "$SP_2$" in FIG. 2, and "A," "B," "C," and "D" in FIG. 3.

TES does not have a good capability to target specific locations in the brain for stimulation, due primarily to the fact that the stimulating current must pass through bone which is not very conductive. So in general, again referring particularly to FIG. 3, the target 18 would be too small for differential stimulation of the subpopulations A-D were it not for the fact that the cortex is wrinkled. The present inventors have recognized that cortical wrinkling allows for differential stimulation of subpopulations using TES, not by targeting specific locations in the cortex, but by targeting specific orientations of the cortical surface. Further, this type of targeting is based on a recognition that any given neuron is most effectively stimulated when the stimulating current is injected normal to the cortical surface where the neuron is located, i.e., parallel to the neuron's dipolar axis, and that the neuron will not as a practical matter be effectively synchronized with an injected stimulating current that deviates from the surface normal by more than a predetermined amount.

The maximum angle of misalignment or deviation between the cortical surface normal of a neuron and the direction a stimulating current is injected into the neuron will be referred to as the "angular stimulation range." Preferably, this range is less than or equal to 45 degrees; more preferably it is less than or equal to 30 degrees, and more preferably it is less than or equal to 20 degrees.

The angular stimulation range can be used according to the invention for identifying potential subpopulations for selective synchronization or stimulation.

Subpopulations may be identified as being localized groups of neurons within which the surface normal vectors for all the neurons lie inside the angular stimulation range. To provide a simplified illustration of this, FIGS. 2 and 3 show aggregate surface normal vectors that are representative for the subpopulations shown; in FIG. 2, aggregate surface normal vectors "$SN_1$" and "$SN_2$" for the subpopulations $SP_1$ and $SP_2$, and in FIG. 3, aggregate surface normals "$SN_A$" for the subpopulation A, "$SN_B$" for the subpopulation B, "$SN_C$" for the subpopulation C, and "$SN_D$" for the subpopulation D. It is to be understood that, since the cortical surface 18a is not planar, the surface normal vectors for each infinitesimal or "differential" portion of the surface of even a relatively small subpopulation will not everywhere be parallel to the aggregate surface normal vectors. With particular reference to FIG. 3, examples of such differential surface normal vectors are shown as "DSN" in connection with the subpopulation A. The aggregate surface normal vectors may be an average, e.g., they may be a mean, median, or integral average, of the differential surface normal vectors DSN.

According to the invention, if all the differential surface normal vectors of a contiguous surface area of the cortex are within the angular stimulation range, that surface area may be considered to define a subpopulation of neurons.

FIG. 3 also illustrates how to distinguish one subpopulation from another according to the invention. It shows aggregate surface normal vectors (again, as illustrative proxies for individual differential surface normal vectors) that make angles with each other that are outside of the angular stimulation range and which are therefore "distinct" from each other. More particularly, the aggregate surface normal vector $SN_A$ for the subpopulation A makes an angle $\theta_{AB}$, with the aggregate surface normal vector $SN_B$ for the subpopulation B, that is outside the preferred 20 degree angular stimulation range. Likewise the angles $\theta_{AC}$, $\theta_{AD}$, $\theta_{BD}$, and $\theta_{CD}$ are substantially greater than 20 degrees.

By contrast, the aggregate surface normal vectors (not shown) for the subpopulations labeled "E" and "F" in FIG. 3 are nearly parallel to each other as well as to the aggregate surface normal vector for the subpopulation C, and are therefore well within the angular stimulation range and not distinct from each other. Stimulating any one of these subpopulations will stimulate the other two, and the three subpopulations can be considered for purposes herein as being the same.

The identified subpopulations form a pool, from which at least two subpopulations having distinct differential surface normal vectors may be selected, for selective synchronization with targeted stimulating currents. The stimulating currents would preferably be targeted to align with the aggregate surface normal vectors NA for the selected subpopulations.

The source currents used for stimulating the at least two selected subpopulations may be applied over the same periods of time, or during different periods of time, or any desired combination of the two. Moreover, the source current(s) used for stimulating a given selected subpopulation may be applied repetitively, and/or in either a regular or a randomized sequence with the source current(s) used for stimulating the remaining ones of the selected subpopulations.

It has so far been assumed that the pattern and density of the electrodes 12 will allow for differentially stimulating the selected subpopulations, i.e., by injecting one or more currents within the angular stimulation range for a given one of the selected subpopulations, and outside the angular stimulation ranges of the remaining ones of the selected subpopulations. But this may not be the case. The pattern and density of the electrodes will in general be a constraint on the selection of the subpopulations to be stimulated, and may be a constraint on the initial identification of potential subpopulations for stimulation.

To account for this, methods according to the invention may include constructing an electrical head model for the subject, and using the electrical head model to predict current injection paths for different pairings of the electrodes provided in a given pattern and density, to determine pairings of electrodes that can be used to optimally differentially stimulate the greatest number of distinct subpopulations, and/or to optimally define a pattern and density of electrodes to be used. As is typical in the art, the head model may be obtained by combining MRI, X-ray computed tomography ("CT"), and electrical impedance tomography ("EIT") of the subject's head.

It is to be understood that, while a specific method for desynchronizing pathological neural oscillations has been shown and described as preferred, other configurations and methods could be utilized, in addition to those already mentioned, without departing from the principles of the invention.

The terms and expressions which have been employed in the foregoing specification are used therein as terms of description and not of limitation, and there is no intention in the use of such terms and expressions to exclude equivalents of the features shown and described or portions thereof, it being recognized that the scope of the invention is defined and limited only by the claims which follow.

The invention claimed is:

1. A method for desynchronizing a pathological neural oscillation in the brain of a subject, the brain having a cortex and the neurons involved in the pathological neural oscillation extending to the cortex, the method comprising:
   identifying a first contiguous subset of the cortex wherein first neurons involved in the pathological neural oscillation are (A) in alignment with each other within a predetermined angular stimulation range;
   identifying a second contiguous subset of the cortex, distinct from the first contiguous subset of the cortex, wherein second neurons that are also involved in the pathological neural oscillation are both (A) in alignment with each other within the predetermined angular stimulation range, and (B) out of alignment with the first neurons by at least said predetermined angular stimulation range;
   applying, through a first set of scalp electrodes, a first electrical stimulus to the first subset of the cortex that is in alignment with the first neurons within said predetermined angular range, and which is out of phase with the pathological neural oscillation; and
   applying, through a second set of scalp electrodes, a second electrical stimulus to the second subset of the cortex that is in alignment with the second neurons within said predetermined angular range, and which is out of phase with the pathological neural oscillation, wherein the steps of applying the first and second stimuli are sufficient to desynchronize the pathological neural oscillation.

2. The method of claim 1, wherein the second electrical stimulus is out of phase with the first electrical stimulus.

3. The method of claim 1, wherein the first and second electrical stimuli are applied during overlapping times.

4. The method of claim 1, at least one of said steps of identifying contiguous subsets of the cortex comprises obtaining an electroencephalographic signature of the pathological neural oscillation.

5. The method of claim 1, further comprising creating a model of electrical properties of the subject's head, and utilizing the model for determining at least one of the first and second electrical stimuli.

6. The method of claim 5, wherein said step of creating a model of electrical properties of the subject's head comprises combining data obtained from magnetic resonance imaging, X-ray computed tomography, and electrical impedance tomography performed on the subject's head.

7. The method of claim 1, further comprising obtaining a magnetic resonance image of the subject's head, and utilizing the magnetic resonance image for predetermining, relative to said step of applying the first electrical stimulus, whether the first neurons satisfy criterion (A).

8. The method of claim 6, further comprising utilizing the magnetic resonance image for predetermining, relative to said step of applying the second electrical stimulus, whether the second neurons satisfy both criteria (A) and (B).

* * * * *